(12) United States Patent
Lespine et al.

(10) Patent No.: US 11,130,776 B2
(45) Date of Patent: Sep. 28, 2021

(54) USE OF AVERMECTIN DERIVATIVE FOR INCREASING BIOAVAILABILITY AND EFFICACY OF MACROCYLIC LACTONES

(71) Applicants: INSTITUT NATIONAL DE LA RECHERCHE AGRONOMIQUE, Paris (FR); THE ROYAL INSTITUTION FOR THE ADVANCEMENT OF LEARNING/MCGILL UNIVERSITY, Montreal (CA)

(72) Inventors: Anne Lespine, Toulouse (FR); Roger Prichard, Toulouse (FR); Cecile Menez, Toulouse (FR)

(73) Assignees: INSTITUT NATIONAL DE RECHERCHE POUR L'AGRICULTURE, L'ALIMENTATION ET L'ENVIRONNEMENT; THE ROYAL INSTITUTION FOR THE ADVANCEMENT OF LEARNING/MCGILL UNIVERSITY

( * ) Notice: Subject to any disclaimer, the term of this patent is extended or adjusted under 35 U.S.C. 154(b) by 0 days.

(21) Appl. No.: 14/352,669

(22) PCT Filed: Oct. 18, 2012

(86) PCT No.: PCT/EP2012/070704
§ 371 (c)(1),
(2) Date: Apr. 17, 2014

(87) PCT Pub. No.: WO2013/057222
PCT Pub. Date: Apr. 25, 2013

(65) Prior Publication Data
US 2014/0256619 A1    Sep. 11, 2014

(30) Foreign Application Priority Data
Oct. 18, 2011 (EP) .................................. 11306348

(51) Int. Cl.
| | |
|---|---|
| *A01N 37/18* | (2006.01) |
| *A61K 38/00* | (2006.01) |
| *A61K 45/06* | (2006.01) |
| *A61P 25/08* | (2006.01) |
| *A61P 31/12* | (2006.01) |
| *A61P 33/00* | (2006.01) |
| *A61P 35/00* | (2006.01) |
| *C07H 17/08* | (2006.01) |
| *A61K 31/7048* | (2006.01) |
| *A61K 31/277* | (2006.01) |
| *A61K 31/365* | (2006.01) |
| *A61K 31/475* | (2006.01) |
| *A61K 31/366* | (2006.01) |
| *C07D 493/06* | (2006.01) |
| *C07D 493/20* | (2006.01) |

(52) U.S. Cl.
CPC ........... *C07H 17/08* (2013.01); *A61K 31/277* (2013.01); *A61K 31/365* (2013.01); *A61K 31/366* (2013.01); *A61K 31/475* (2013.01); *A61K 31/7048* (2013.01); *A61K 45/06* (2013.01); *C07D 493/06* (2013.01); *C07D 493/20* (2013.01)

(58) Field of Classification Search
CPC .... A01N 37/18; A61K 38/00; A61K 2300/00; A61K 31/277; A61K 31/365; A61K 31/475; A61K 31/7048; A61K 31/366; A61K 45/06; A61P 25/08; A61P 31/04; A61P 31/12; A61P 33/00; A61P 35/00
See application file for complete search history.

(56) References Cited

U.S. PATENT DOCUMENTS

| | | | |
|---|---|---|---|
| 5,595,756 A * | 1/1997 | Bally | ................... A61K 9/1272 264/4.1 |
| 5,778,436 A | 7/1998 | Kedem et al. | |
| 6,182,198 B1 | 1/2001 | Hubis et al. | |
| (Continued) | | | |

FOREIGN PATENT DOCUMENTS

| | | |
|---|---|---|
| AU | 2005202712 A1 | 7/2005 |
| CA | 2778431 A1 | 5/2011 |
| (Continued) | | |

OTHER PUBLICATIONS

Andrews, Pharma. Ther., 1985, vol. 29, pp. 129-156.*
Foley et al., Transactions of the Royal Society of Tropical Medicine and Hygiene, 2000, 94, 625-628.*
Chemspider, available online at: http://www.chemspider.com/Chemical-Structure.16738655.html, accessed on Jun. 8, 2015.*
Andrews, Pharma. Ther., 1985, vol. 29, pp. 129.*
Sheriff et al., Parasitology, 2002, 125, 477-484.*
Bioaustralis, Ivermectin aglycone, Product Data Sheet, Bioaustralis Fine Chemicals, Mar. 9, 2008.*
(Continued)

*Primary Examiner* — Julie Ha
(74) *Attorney, Agent, or Firm* — McBee Moore & Vanik, IP, LLC

(57) ABSTRACT

The present invention relates to the use of avermectin derivative as a drug for the treatment of parasitic infections. The avermectin derivative is represented by the formula (I) wherein: (i) $R_1$ is chosen from the group constituted of —CH(CH$_3$)$_2$, —CH(CH$_3$)CH$_2$CH$_3$, or cyclohexyle, (ii) X represents —CH$_2$—CH$_2$—, or —CH=CH—, (iii) $R_2$ is chosen from the group constituted of or —OH group, (iv) $R_3$ is OH or NOH, (v) represents a single bond when $R_3$ is OH, or a double bond when $R_3$ is NOH, as an inhibitor of a membrane-bound protein which transports exogenous compounds out of target cells.

10 Claims, 6 Drawing Sheets

(56) References Cited

U.S. PATENT DOCUMENTS

| | | | |
|---|---|---|---|
| 6,434,681 B1 | 8/2002 | Armangau | |
| 6,489,303 B2 | 12/2002 | Jancys | |
| 6,694,413 B1 | 2/2004 | Mimatsu et al. | |
| 6,711,662 B2 | 3/2004 | Peir et al. | |
| 7,035,881 B2 | 4/2006 | Tummala et al. | |
| 7,165,145 B2 | 1/2007 | Lam | |
| 7,225,210 B2 | 5/2007 | Guthrie, II | |
| 7,257,606 B2 | 8/2007 | Kapoor et al. | |
| 7,296,125 B2 | 11/2007 | Ohran | |
| 7,363,435 B1 | 4/2008 | Stenstrom | |
| 7,426,618 B2 | 9/2008 | Vu et al. | |
| 7,434,093 B2 | 10/2008 | Ohran | |
| 7,440,966 B2 | 10/2008 | Adkins et al. | |
| 7,671,034 B2 * | 3/2010 | Freehauf | A23K 20/121 514/30 |
| 7,676,510 B1 | 3/2010 | Karinta | |
| 7,676,514 B2 | 3/2010 | Faibish et al. | |
| 7,734,591 B1 | 6/2010 | Mercier et al. | |
| 7,751,348 B2 | 7/2010 | Shaffer et al. | |
| 7,757,057 B2 | 7/2010 | Sangapu et al. | |
| 7,792,802 B1 | 9/2010 | Rao | |
| 7,870,356 B1 | 1/2011 | Veeraswamy et al. | |
| 7,886,119 B1 | 2/2011 | Cameron et al. | |
| 8,281,096 B1 | 10/2012 | Ranade | |
| 8,364,639 B1 | 1/2013 | Koryakina et al. | |
| 8,402,008 B2 | 3/2013 | Adkins et al. | |
| 8,533,409 B2 | 9/2013 | Schnapp et al. | |
| 8,874,524 B1 | 10/2014 | Zhao et al. | |
| 8,880,820 B2 | 11/2014 | Sudhakar et al. | |
| 9,218,139 B2 | 12/2015 | Ammons et al. | |
| 9,298,633 B1 | 3/2016 | Zhao et al. | |
| 2002/0028780 A1 | 3/2002 | Lukas et al. | |
| 2003/0064941 A1 | 4/2003 | Bishop | |
| 2003/0158834 A1 | 8/2003 | Sawdon et al. | |
| 2004/0151744 A1 * | 8/2004 | Bishop | A01N 43/90 424/400 |
| 2005/0033930 A1 | 2/2005 | Haruma et al. | |
| 2007/0055710 A1 | 3/2007 | Malkin | |
| 2007/0130228 A1 | 6/2007 | Breau et al. | |
| 2007/0174569 A1 | 7/2007 | Schnapp et al. | |
| 2009/0187719 A1 | 7/2009 | Yao et al. | |
| 2010/0241614 A1 | 9/2010 | Shaull et al. | |
| 2012/0089578 A1 | 4/2012 | Lam | |
| 2014/0281123 A1 | 9/2014 | Weber | |
| 2017/0290882 A1 * | 10/2017 | Andronova | A61K 31/7068 |
| 2017/0360955 A1 * | 12/2017 | Janssen | A61K 51/1018 |

FOREIGN PATENT DOCUMENTS

| | | |
|---|---|---|
| CA | 2793880 A1 | 10/2011 |
| EP | 1632498 A1 | 3/2006 |
| WO | WO2001/070028 | 9/2001 |
| WO | WO2008/136791 | 11/2008 |
| WO | WO 2011/015220 A1 | 2/2011 |
| WO | 2011/054103 A1 | 5/2011 |

OTHER PUBLICATIONS

Merck Sharp & Dohme Corp., tablets STROMECTOL (ivermectin) description, issued on May 2010.*
Metabolism of Ivermectin, Environmental Impact Analysis Report, IVOMEC® (Ivermectin) Injection for Cattle, Merck Sharp & Dohme Research Laboratories, 1983, p. 38.*
Steel, Vet Parasitol, 1993, 48(1-4), 45-57.*
Heartguard, Veterinary Product and Label Information, 2010, available online at: https://vetlabel.com/lib/vet/meds/heartgard/.*
Bioaustralis Fine Chemicals, Bioaustralis Fine Chemicals, Ivermectin Aglycone, Product Data Sheet, created on Mar. 9, 2008.*
Komarova et al., PNAS, Jul. 5, 2005, 9714-9719. (Year: 2005).*
Mitchell et al., Dalmatian Club of America—A Basic Overview of Seizures Their Cause and Treatment, May 6, 2003. (Year: 2003).*
Hait, WN, "Anticancer drug development: the grand challenges," Nature Reviews, Apr. 2010, 9: 253-254. (Year: 2010).*
Spom et al, "Chemoprevention," 2000, 21(3): 525-530. (Year: 2000).*
Auerbach etal, "Angiogenesis assays: Problems and pitfalls," Cancer and Metastasis Reviews, 2000, 19: 167-172. (Year: 2000).*
Gura T., "Systems for Identifying New Drugs Are Often Faulty," Science, 1997, 278: 1041-1042. (Year: 1997).*
Jain RK, "Barriers to Drug Delivery in Solid Tumors," Scientific American, 1994, 58-65. (Year: 1994).*
Neidle, Stephen, ed., "Failure Modes in the Discovery Process," Cancer Drug Design and Discovery, 2008, 427-431. (Year: 2008).*
Asio et al., "A randomized, double-blind field trial of ivermectin alone and in combination with albendazole for the treatment of Mansonella perstans infections in Uganda," Transactions of the Royal Society of Tropical Medicine and Hygiene, 2009, pp. 274-279, 103(3).
Banks et al., "Avermectins and flea control: structure-activity relationships and the selection of selamectin for development as an endectocide for companion animals," Bioorganic and Medicinal Chemistry, 2000, pp. 2017-2025, 8(8).
Dawson et al., "Anticonvulsant and adverse effects of avermectin analogs in mice are mediated through the gamma-aminobutyric $acid_A$ receptor," J of Pharmacology and Experimental Therapeutics, 2000, 1051-1060, 295(3).
Deng et al., "House fly head GABA-gated chloride channel: Toxicologically relevant binding site for avermectins coupled to site for ethynylbicycloorthobenzoate," Pesticide Biochem and Physiology, 1992, pp. 116-122, 43(2).
Denham et al., "The Effects of Some Avermectins on the Growth of Brugia pahangi," Methods and Findings in Experimental and Clinical Pharmacology, 1982, pp. 347-350, 4(5).
Fisher et al., "The chemistry and pharmacology of avermectins," Annual Review of Pharmacology and Toxicology, 1992, pp. 537-553, 32.
Furusawa et al., "Potentiation of doxorubicin-induced apoptosis of resistant mouse leukaemia cells by ivermectin," Pharmacy and Pharmacology Communications, 2000, pp. 129-134, 6(3).
Kotze, "Effects of macrocyclic lactones on ingestion in susceptible and resistant Haemonchus contortus larvae," J of Parasitology, 1998, pp. 631-635, 84(3).
Lespine et al., "ABC transporter modulation: a strategy to enhance the activity of macrocyclic lactone anthelmintics," Trends in Parasitology, 2008, pp. 293-298, 24(7).
Lespine et al., "Interaction of ivermectin with multidrug resistance proteins (MRP1, 2 and 3)," Chemico-Biological Interactions, 2006, pp. 169-179, 159(3).
Marton Jani et al., "Ivermectin interacts with human ABCG2," J of Pharmaceutical Sciences, 2011, pp. 94-97, 100(1).
Michael et al., "Comparison of ivermectin, doramectin, selamectin, and eleven intermediates in a nematode larval development assay," J of Parasitologists, 2001, pp. 692-696, 87(3).
Pong et al., "Studies on the Mechanism of Action of Avermectin $B_1a$: Stimulation of Release of gamma-Aminobutyric Acid from Brain Synaptosomes," J of Neurochemistry, 1980, pp. 351-358, 34(2).
Schulz-Key, "Observations on the reproductive biology of Onchocerca volvulus," Acta Leidensia, 1990, pp. 27-44, 59(1-2).
Sheriff et al., "Effect of ivermectin on feeding by Haemonchus contortus in vivo," Vet. Parasitology, 2005, pp. 341-346, 128(3-4).
Sheriff et al., "Effects of macrocyclic lactone anthelmintics on feeding and pharyngeal pumping in Trichostrongylus colubriformis in vitro," Parasitology, 2002, pp. 477-484, 125(5).
Shoop et al., "Efficacy in sheep and pharmacokinetics in cattle that led to the selection of Eprinomectin as a topical endoctocide for cattle," International J of Parasitology, 1996, pp. 1227-1235, 26(11).
Shoop et al., "Avermectins and milbemycins against Fasciola hepatica: In vivo drug efficacy and in vitro receptor binding," International Journal for Parasitology, 1995, pp. 923-927, 25(8).
Townson et al., "The effects of ivermectin used in combination with other known antiparasitic drugs on adult Onchocerca gutturosa and O. volvulus in vitro," Transactions of the Royal Society of Tropical Medicine and Hygiene, 1990, pp. 411-416, 84(3).
International Search Report, Corresponding to International Application No. PCT/EP2012/070704, dated Jul. 8, 2013.

(56) References Cited

OTHER PUBLICATIONS

International Preliminary Report on Patentability ("IPRP"), issued in PCT/EP2012/070704, dated Apr. 22, 2014.
Borges et al., "Endectocide Activity of a New Long-Action Formulation Containing 2.25% Invermectin+1.25% Abamectin In Cattle Veterinary Parasitology," 155(3-4), pp. 299-307, Aug. 17, 2008 (Aug. 17, 2008) [ISSN: 0304-4017] [doi: 10.1016/j:vetpar. 2008. 04.019].
Dobson et al., "Principles for the Use of Macrocyclic Lactones To Minimise Selection for Resistance;" Australian Veterinary Journal. 79(11), pp. 756-761, Nov. 2001. (Nov. 2001) [ISSN: 0005-0423].
Chabala, et al., "Ivermectin, a New Broad-Spectrum Antiparasitic Agent," J. Med Chem., (1980), vol. 23: 1134-1136.
Shoop, et al., "Structure and activity of avermectins and milbemycins in animal health," Veterinary Parasitology, (1995), vol. 59: 139-156.
Gill, et al., "Detection of Resistance to Ivermectin in Haemonchus Contortus," International Journal for Parasitology, (1991), vol. 21, No. 7: 771-776.
Gill, et al., "Avermectin/milbemycin resistance in trichostrongyloid nematodes," International Journal for Parasitology, (1998), vol. 28: 863-877.
International Search Report dated Jan. 23, 2015 issued in the corresponding Internaitonal PCT Application No. PCT/US14/63889.
Written Opinion of the International Searching Authority dated Jan. 23, 2015 issued in the corresponding International PCT Application No. PCT/US14/63889.
Xiao, et al. "Implementation and performance evaluation of two snapshot methods on iSCSI target storages." Proc. of NASA/IEEE Conference on Mass Storage Systems and Technologies (2006).
W.C. Campbell, ed., "Ivermectin and Abamectin", "IV. Structure-Activity" (M.H. Fisher & H. Mrozik), Springer-Verlag (New York), 1989, p. 16.
Kanbur, Murat et al., "The curative and antioxidative efficiency of doramectin and doramectin+vitamin AD"3E treatment on Psoroptes cuniculi infestation in rabbits", Research in Veterinary Science. Oct. 1, 2008, pp. 291-293, vol. 85, No. 2.
Lespine, Anne et al., "Interaction of macrocyclic lactones with P-glycoprotein: Structure-affinity relationship", European Journal of Pharmaceutical Sciences, Dec. 15, 2006, pp. 84-94, vol. 30, No. 1.
Taverne, M.A.M., "The relation between the birth process and the condition of the newborn piglet and calf", Veterinary Research Communications, 2008, S93-S98, vol. 32 (Suppl 1).
Venkatachalam, Manjeri et al., "Cytoprotection of kidney epithelial cells by compounds that target amino acid gated chloride channels", Kidney International, Feb. 1996, pp. 449-460, vol. 49, Issue 2.
European Search Report of European Patent Application No. 19215890.5 dated Mar. 18, 2021.

\* cited by examiner

USE OF AVERMECTIN DERIVATIVE FOR INCREASING BIOAVAILABILITY AND EFFICACY OF MACROCYLIC LACTONES

CROSS-REFERENCE TO RELATED APPLICATIONS

This application is a U.S. National Stage application under 35 U.S.C. 371 of PCT/EP2012/070704, filed in English on Oct. 18, 2012, which claims priority from European Patent Application No. 11306348.1, filed on Oct. 18, 2011. Each of these applications is incorporated by reference herein in its entirety.

The present invention relates to the use of avermectin derivative in association with macrocyclic lactones as a formulation for the treatment of parasitic infections.

Parasitic infections are the most frequent diseases for livestock or domestic animal. In spite of recent advance in veterinary pharmaceutical research, it is always necessary to find out more efficient and safe drug or formulation to fight against parasitic infections. For humans, the parasitic infections such as onchocerciasis caused by infection by *Onchocerca volvulus*, lymphatic filariasis caused by *Wuchereria bancrofti, Brugia malayi,* and *Brugia timori*, or tropical parasitic diseases are still frequent diseases in developing countries. By the way, though endemic in some developing countries, intestinal strongyloidiasis and cutaneous parasitic diseases also pose a threat to the developed world.

The macrocyclic lactones (ML) are a family of broad spectrum anti-parasitic drugs that was developed in early 80s and have been widely used for the treatment of both internal and external parasites in pets, in livestock and in humans. MLs are also efficient for treating parasitic diseases caused by benzimidazole-, levamisole-, and pyrantel-resistant strains of nematodes.

MLs are a family of compounds isolated from soil microorganisms belonging to the genus *Streptomyces*. Macrocyclic lactones comprise avermectins and milbemycins. Avermectins comprise ivermectin, abamectin, doramectin, eprinomectin or selamectin, while milbemycins comprise moxidectin, nemadectin, and milbemycin oxime.

The principal action of MLs in parasitic nematodes is to increase membrane permeability to chloride ions by interacting with the glutamate-gated chloride channel subunit. The glutamate and γ-aminobutyric acid (GABA)-agonist activities of the MLs are the mechanisms that lead to the paralysis and death of the treated parasites at nanomolar concentration. In fact, MLs maintain open the glutamate-gated channels that blocks pharyngeal pumping and inhibits of feeding, which is one of the effects that cause the death of parasite. By the way, ivermectin leads also to activation and paralysis of body muscle in *Haemonchus contortus* (Sheriff et al., *Vet. Parasitol.,* 2005, 128(3-4), 341-346), and inhibits worm reproduction in *Onchocerca volvulus* (Schulz-Key, *Acta Leiden,* 1990, 59(1-2), 27-44).

However, in the last years, widespread MLs resistance has been observed in some nematode parasites of sheep, goats and cattle. The cause and mechanism of MLs resistance are yet not completely understood, but recent research has showed that MDR (multidrug resistance) transporters are a group of protein implied in the MLs resistance. MDR transporters are membrane proteins belonging to the ABC (ATP binding cassette) family, and whose main function is the ATP-dependent transport of a number of structurally unrelated exogenous compounds. Due to their expression in the plasma membrane, they function as a permeability barrier for the passage of xenobiotic across the cell membrane by actively expelling them out of the cells. MDR transporters have been considered as one of the causes of chemotherapy effectiveness restriction, when the tumor cells overexpress these transporters. MDR transporters also limit the entry of MLs into human target organism and affect the efficiency of MLs as antiparasitic. In addition, the expression of MDR transporters in intestine, liver and kidney allows them to detoxify these tissues, and ultimately eliminate the substrate drugs out of the systemic circulation, exerting a protecting action against their toxicity but also restricting their therapeutic efficacy.

P-glycoprotein (Pgp), localized in the apical membrane, is one of MDR transporters. The main function of Pgp is the active efflux of various structurally unrelated exogenous compounds to protect both vertebrate and invertebrate organisms against potentially toxic molecules. Pgp can transport its substrate from the baso-lateral side to the apical side of epithelia and endothelia. Pgp plays also an important role in blood-brain barrier, since it can limit the concentration of xenobiotics in the brain. The overexpression of Pgp is one of cause of drug resistance observed during avermectin treatment for parasitic infections or some tumor chemotherapy.

Later, other multidrug resistance proteins MRP1, 2 and 3 (ABCC1, 2 and 3) are also discovered. They are also involved in multidrug resistance and provide complementary and overlapping activities as multispecific drug efflux pumps The more recently discovered Breast Cancer Resistance protein is ABCG2, which assists Pgp to prevent unwanted material in the circulation from passing into the brain. Homologues of MDR transporters exist also in parasite, and the selection and/or modulation of expression of their gene could be one of the reasons of the resistance of parasite to MLs.

Different methods have been developed in the past years to overcome the effectiveness restriction due to the efflux pumps of administrated drug. One of them is the use of MDR transporters inhibitors which can block efflux pumps of administrated drugs to improve intracellular concentration of active ingredient. Some Pgp ligands have been reported in the past, such as cyclosporine A, its derivative PSC833 (Valspodar®), the antidiarrheal opioid drug loperamid, or verapamil. However, unfortunately, till today, because of important toxicity of these MDR transporters inhibitors, neither of them can be applied in pharmaceutical use.

MLs have been firstly observed as substrates of MDR transporters. Later, it was found that MLs, in particular ivermectin, are also inhibitors of MDR transporters.

In spite of the fact that ivermectin can efficiently inhibit MDR transporters, it can not become a candidate drug, because of its important neurotoxicity if it penetrates in the brain at high concentration. In fact, ivermectin interacts with GABA receptors, a complex situated in nervous system. The abnormal function of GABA receptors can lead to neurologic, mental, vegetotropic, somatic, hormonal and other disorders. Since inhibition of MDR transporters is still the most promising method to restrain chemotherapy resistance; and macrocyclic lactone are still key molecules for treating parasitic infections, it is necessary and urgent to find new safe and efficient inhibitors of MDR transporters.

The objective of the present invention is to provide an inhibitor of multidrug resistance proteins.

Particularly, the present invention concerns the use of an avermectin derivative compound of formula I

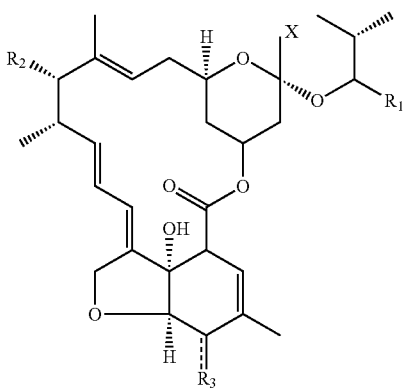

wherein:
(i) R₁ is chosen from the group constituted of —CH(CH₃)₂, —CH(CH₃)CH₂CH₃, or cyclohexyl,
(ii) X represents —CH₂—CH₂—, or —CH=CH—,
(iii) R₂ is chosen from the group constituted of

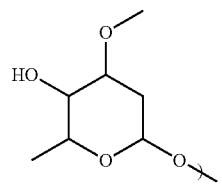

or —OH group,
(iv) R₃ is OH or NOH,
(v) ----- represents a single bond when R₃ is OH, or a double bond when R₃ is NOH, as an inhibitor of a membrane-bound protein which transports exogenous compounds out of target cells.

When R₂ represents —OH group, the compound of formula I is an aglycone avermectin.

When R₂ represents

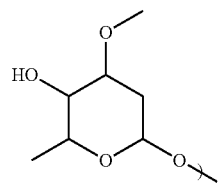

the compound of formula I is a monosaccharides of avermectin.

The Inventors of the present invention have surprisingly observed that aglycone avermectins or monosaccharide of avermectins expose a comparable inhibitory potency and efficiency with that of ivermectin or Valspodar®, the last is one of the most efficient MDR inhibitors already known. Moreover, the Inventors have observed that aglycone avermectins or monosaccharide of avermectins have a higher inhibitory potency for nematode Pgp than that for murine Pgp. This particularity enables aglycone avermectin or monosaccharide of avermectins to be used as adjuvant for conventional antiparasitic, which suffer from an efficiency restriction due to efflux pump by intermediate of Pgp of parasite. The most surprisingly, aglycone avermectins or monosaccharide of avermectins exhibit a weak agonist for GABA receptors, which means that aglycone avermectins have weaker neurotoxicity compared to avermectin, especially ivermectin.

"A membrane-bound protein which transports exogenous compounds out of target cells" can be a membrane-bound ATP-binding cassette (ABC) transporter protein which mediates cellular efflux of distinct drugs or chemicals of a wide variety of structure and function. Particularly, such membrane-bound protein can be P-glycoprotein (ABCB1), multidrug resistance associated protein family, including MRP1/ABCC1, MRP2, MRP2, or breast cancer resistant protein (ABCG2).

The inhibitor of such membrane-bound protein is a compound which can bind to said membrane-bound protein and thus reduce the affinity of said membrane-bound transporter with another substrate. The inhibitory potency of an inhibitor can be measured according to any conventional method, such as using a reference fluorescent substrate (ex: rhodamine 123 for Pgp) of the transporter and by measuring the intracellular accumulation of this substrate.

Another aspect of the present invention concerns the use of a compound of formula I, as adjuvant for increasing bioavailability of an active ingredient of a drug whose efflux out of target cells depends on a membrane-bound protein which transports exogenous compounds out of target cells.

The term "adjuvant" refers to a molecule which has no therapeutic potency when it is administrated alone, but can improve therapeutic potency of another molecule when it is simultaneously administrated with said another molecule.

The avermectin derivative compound of the present invention, which efficiently inhibits a membrane-bound protein, in particular ABC proteins, enables to improve intracellular concentration of the active ingredient of a drug, consequently, to restore or improve efficiency of said drug.

More particularly, the present invention is related to avermectin derivative compounds of formula I:

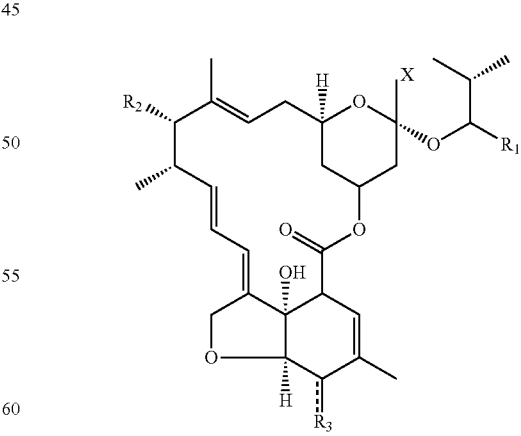

wherein:
(i) R₁ is chosen from the group constituted of —CH(CH₃)₂, —CH(CH₃)CH₂CH₃, or cyclohexyl,
(ii) X represents —CH₂—CH₂—, or —CH=CH—, (iii) $R_2$ is chosen from the group constituted of

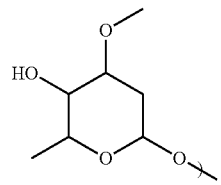

or —OH group, (iv) $R_3$ is OH or NOH, (v) ----- represents a single bond when $R_3$ is OH, or a double bond when $R_3$ is NOH, for its use as an adjuvant of a drug.

In one particular embodiment, the invention concerns an avermectin derivative compound of formula I for its aforementioned use, wherein:

(i) R1 is chosen from the group constituted of —CH(CH$_3$)$_2$ and —CH(CH$_3$)CH$_2$CH$_3$, (ii) X represents —CH$_2$—CH$_2$—, (iii) $R_2$ is —OH, (iv) ----- $R_3$ is —OH, said compound corresponding to ivermectin aglycone of formula I(a):

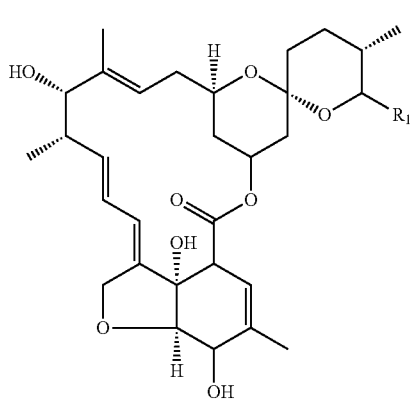

(Ia)

In another particular embodiment, the invention concerns an avermectin derivative compound of formula I for its aforementioned use, wherein:

(i) R1 is chosen from the group constituted of —CH(CH$_3$)$_2$, and —CH(CH$_3$)CH$_2$CH$_3$, (ii) X represents —CH$_2$—CH$_2$—, (iii) R2 is

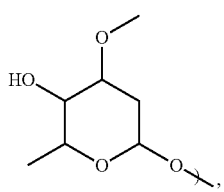

(iv) ----- $R_3$ is —OH, said compound corresponding to monosaccharide of ivermectin of formula I(b).

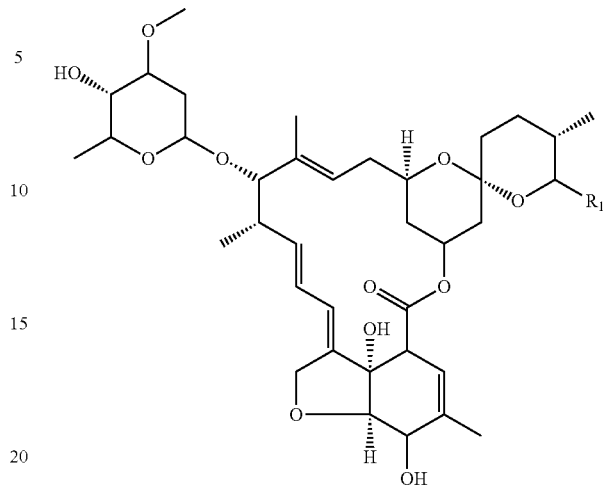

I(b)

In another particular embodiment, the invention concerns an avermectin derivative compound of formula I for its aforementioned use, wherein:

(i) R1 is chosen from the group constituted of —CH(CH$_3$)$_2$, and —CH(CH$_3$)CH$_2$CH$_3$, (ii) X represents —CH=CH—, (iii) $R_2$ is —OH, (iv) ----- $R_3$ is —OH, said compound corresponding to formula I(c):

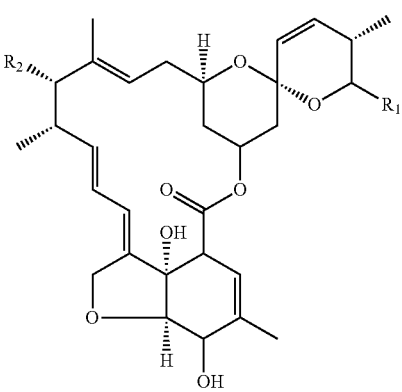

I(c)

A compound of formula I(c) can be eprinomectin aglycone, eprinomectin monosaccharide, emamectine aglycone, emamectine monosaccharide, abamectine aglycone or abamectine monosaccharide.

In another particular embodiment, the invention concerns an avermectin derivative compound of formula I for its aforementioned use, wherein:

(i) R1 is cyclohexyl, (ii) X represents —CH=CH—, (iii) $R_2$ is —OH,

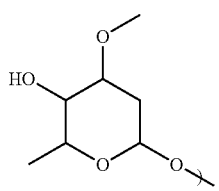

(iv) ---- R$_3$ is —OH, said compound corresponding to doramectin monosaccharide or doramectine aglycone of formula I(d):

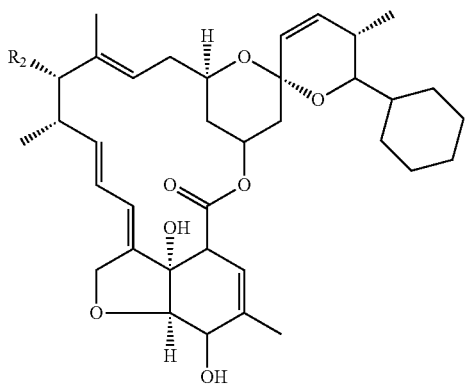

In another particular embodiment, the invention concerns an avermectin derivative compound of formula I for its aforementioned use, wherein:
(i) R1 is cyclohexyl,
(ii) X represents —CH$_2$—CH$_2$—,
(iii) R$_2$ is —OH or

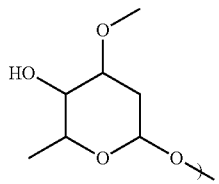

(iv) ---- R$_3$ is =NOH, said compound corresponding to selamectin or selamectin aglycone of formula I(e):

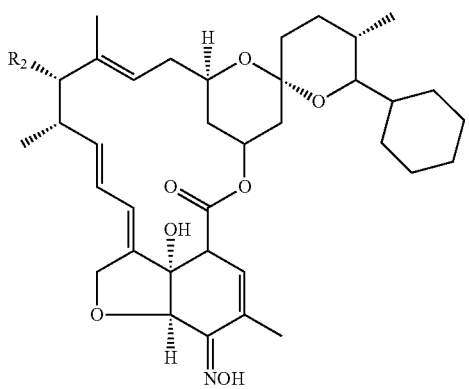

In one particular embodiment, the avermectin derivative compound of the present invention is used as an adjuvant of an active ingredient chosen from the group comprising an antiparasitic, an antitumor agent, an antiviral agent, an anti-epileptic agent, an antibacterial agent, in particular an antibiotic, an antifungal or any compound which is substrate of said membrane-bound protein.

Such active ingredient can be any active ingredient used in an antiparasitic, antitumor agent, antiviral agent, or anti-epileptic agent known in the art.

In one particular embodiment, the antiparasitic is chosen from the group comprising macrocylic lactones, such as the avermectins, in particular ivermectin, abamectin, doramectin, eprinomectin or selamectin, or the milbemycins, in particular moxidectin, nemadectin, or milbemycin oxime.

In another particular embodiment, the antitumor agent is chosen from the group comprising:
  antibiotic antitumor of type anthracycline, such as daunurubicin, doxorubicin, mitocycin C, mitoxantron, adriamycin, and actinomycin, or
  taxanes, such as docetaxel, paclitaxel, or
  alcaloides, such as vinblastin, vincristin, or
  epipodophyllotoxins, such as etoposide, irinotecan, teniposide, and topotecan.

In another particular embodiment, the antiviral agent is chosen from the group comprising: HIV-1 protease inhibitors, ritonavir, saquinavir, nelfinavir and indinavir and non-nucleoside reverse-transcriptase inhibitors such as efavirenz.

In another particular embodiment, the anti-epileptic agent is chosen from the group comprising: Phenobarbital (PB; 5-ethyl-5-phenyl-2,4,6-trioxohexahydropyrimidine), topiramate, lamotrigine phenytoin (PHT; 5,5-diphenyl-2,4-imidazolidinedione), and carbamazepine (CBZ; 5H-dibenz[b,f]azepine-5-carboxamide).

In another particular embodiment, the antibacterial agent can be an antibiotic, such as loperamide, monensin, or the macrolides.

In another particular embodiment, the antifungal agent is chosen from an azole antifungal, such as itraconazole or ketoconazole.

Another aspect of the present invention is to provide a composition comprising a compound of formula I, in particular I(a), I(b), I(c), I(d) or I(e) for its use as drug.

Particularly, the present invention concerns a composition comprising a compound of formula I, in particular I(a), I(b), I(c), I(d) or I(e) for its use as drug in the treatment of parasite infections, viral infections, chemotherapy resistant cancers, epilepsy, bacterial infections or fungal infections.

The present invention concerns also a synergic composition comprising:
  a compound of formula I, in particular I(a), I(b), I(c), I(d) or I(e),
  an active ingredient chosen from antiparasiticide, an antitumor agent, an antiviral agent, an anti-epileptic agent, an antibacterial agent, in particular an antibiotic, or an antifungal agent.

More particularly, the composition of the present invention comprises:
  a compound of formula I, in particular I(a), I(b), I(c), I(d) or I(e), and
  an active ingredient chosen from an antiparasiticide, an antitumor agent, an antiviral agent, an anti-epileptic agent, an antibacterial agent, in particular an antibiotic, or an antifungal agent, for its use as drug in the treatment of parasite infections, viral infections, chemotherapy resistant cancers, epilepsy, bacterial infections or fungal infections.

The present invention provides also a pharmaceutical composition comprising:
- a compound of formula I, in particular I(a), I(b), I(c), I(d) or I(e), and optionally
- an active ingredient chosen from an antiparasiticide, an antitumor agent, an antiviral agent, an anti-epileptic agent, an antibacterial agent, in particular an antibiotic, or an antifungal agent, and
- a pharmaceutically acceptable carrier.

A pharmaceutically acceptable carrier can be any conventional pharmaceutically acceptable carrier.

The pharmaceutical composition according to the present invention can be used in the treatment of parasite infections, viral infections, chemotherapy resistant cancers, epilepsy, bacterial infections or fungal infections.

The pharmaceutical composition according to the present invention can be administrated by oral route, subcutaneous injection, intravenous injection, or intra-tissue injection.

The pharmaceutical composition according to the present invention can be administrated with a diary dose from 0.01 mg/kg to 0.5 mg/kg The present invention concerns also a kit which is a product containing
- a compound of formula I, and
- an active ingredient chosen from an antiparasitic, an antitumor agent, an antiviral agent, an anti-epileptic agent, an antibacterial agent, in particular an antibiotic, or an antifungal agent, as a combined preparation for simultaneous, separate or sequential use in the treatment of parasite infections, viral infections, chemotherapy resistant cancers, epilepsy, bacterial infections or fungal infections.

The present invention is illustrated in detail by following figures and examples. However, in any way, the figures and the examples can not be considered as a limitation of the scope of the present invention.

FIGURES

Figure 3:
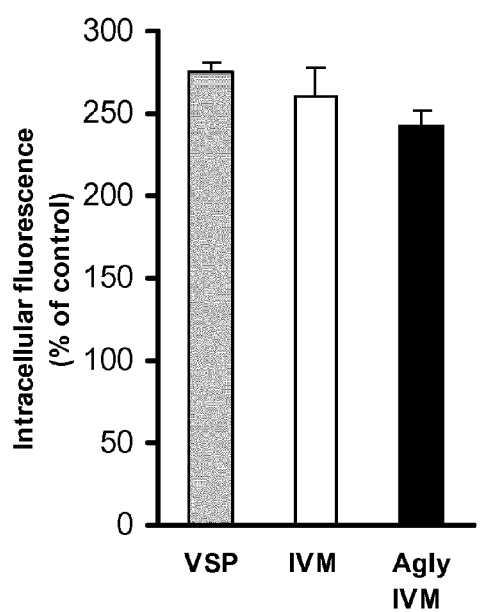

FIG. 3 compares the maximum effective concentration of Valspodar® at 5 µM (VSP, grey column), ivermectin at 5 µM (IVM, white column) and ivermectin aglycone at 10 µM (Agly IVM, black column) in LLCPK1 cells transfected with murine Pgp. Cells are incubated in a buffer containing rhodamine 123 with or without increasing concentrations of drugs and intracellular fluorescence was determined. Y axis represents intracellular fluorescence expressed as percent of the control value (cell incubated without drug). Look at also example 2.2.

Figure 4A:
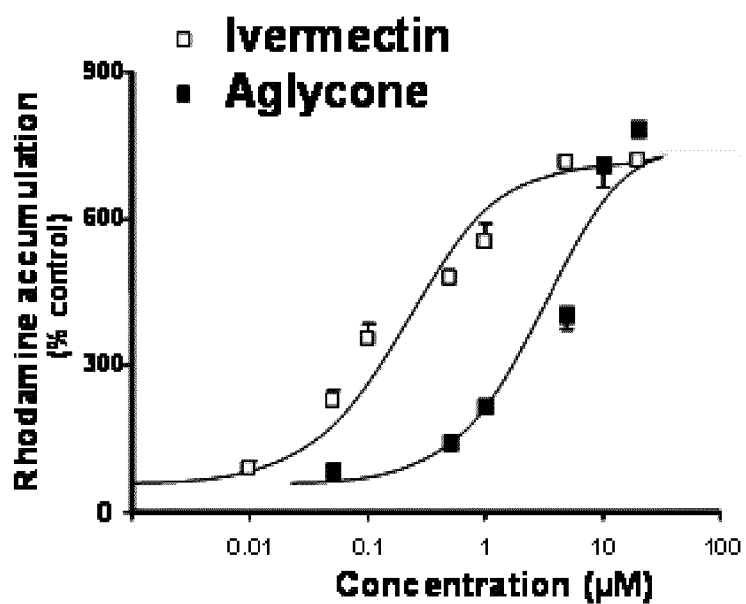

FIG. 4A compares the inhibition of murine Pgp by ivermectin (open square) with that of ivermectin aglycone (black square) in LLC-PK1-mdr1a. X axis represents concentration of ivermectin or ivermectin aglycone. Y axis represents intracellular rhodamine accumulation compared to control value. Look at also example 2.3.

Figure 4B:
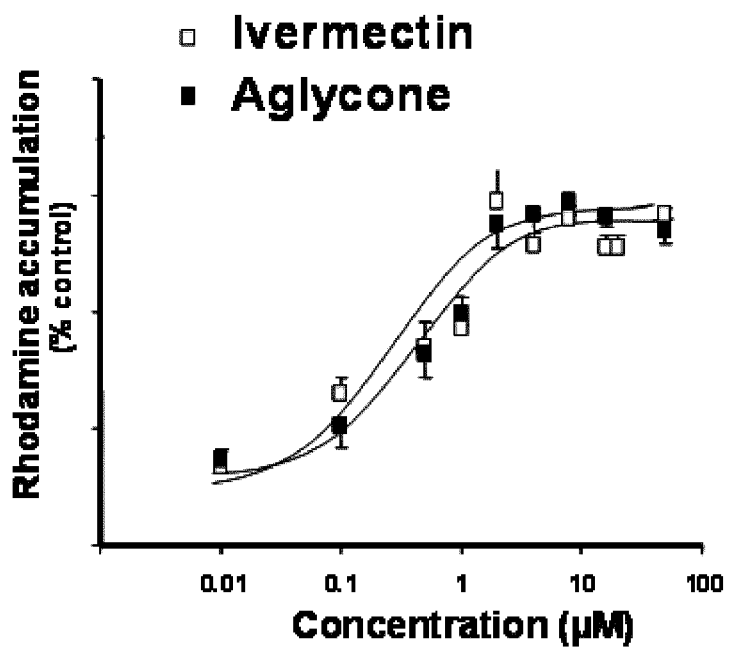

FIG. 4B compares the inhibition of nematode Pgp (HcPgpA) by ivermectin (open square) with that of ivermectin aglycone (black square) in LLC-PK1-HcPgpA. X axis represents concentration of ivermectin or ivermectin aglycone. Y axis represents intracellular rhodamine accumulation compared to control value. Look at also example 2.3.

Figure 5:
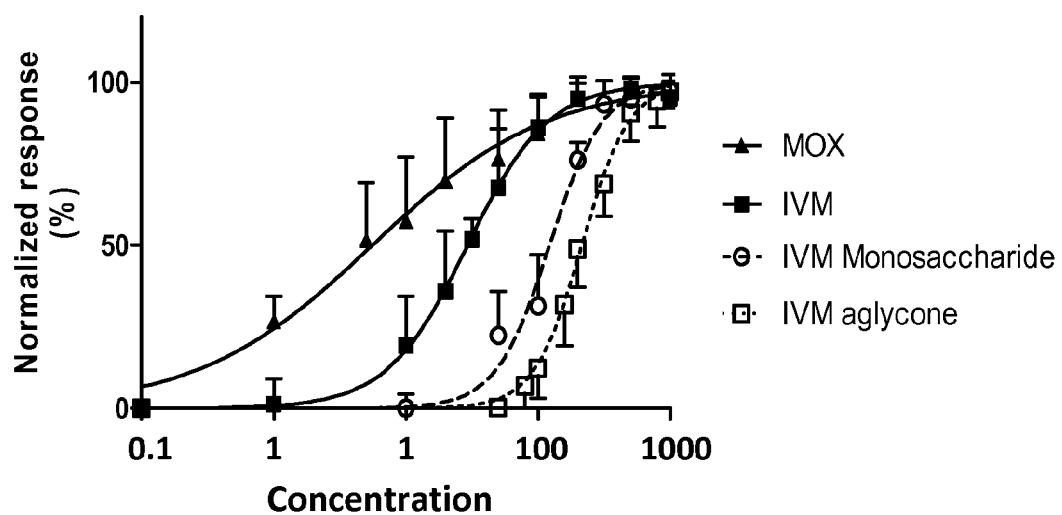

FIG. 5 shows concentration-response curves of rat GABA (A) receptor expressed in *Xenopus* oocytes. Concentration-dependent potentiation of the GABA receptor, presented as the percentage of the GABA-evoked response at $EC_{10}$ (2 µM). Y-axis represents normalized response to GABA receptor according to the protocol described in the part 1.7 below. X-axis represents the concentration of moxidectin (MOX), ivermectin (IVM), ivermectin monosaccharide (IVM Monosaccharide), or ivermectin aglycone (IVM aglycone). Data were fitted to the Hill equation and are given as mean±S.D. Look at also example 2.4

Figure 6:
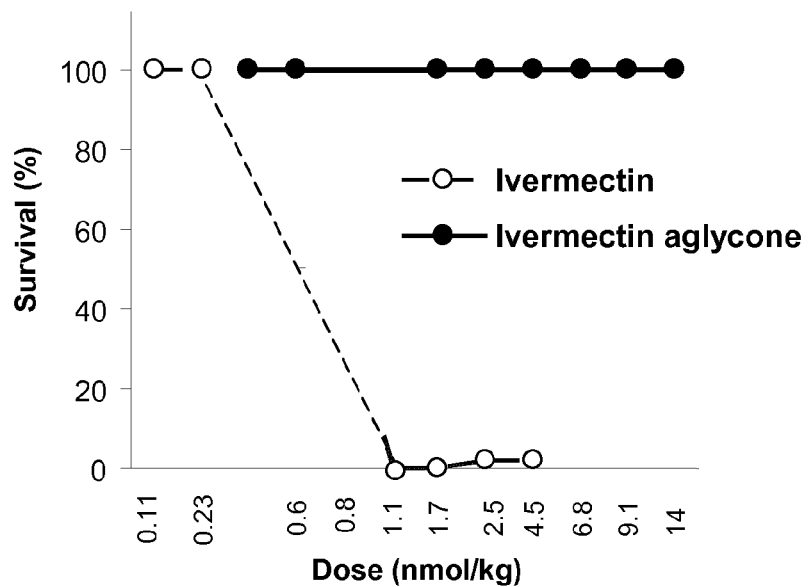

FIG. 6 illustrates toxicity of ivermectin (open circle) and ivermectin aglycone (black circle) in Pgp-deficient mice. X axis represents the dose of ivermectin or ivermectin aglycone administrated to mice. Y axis represents the percentage of survival mice after one week administration. Look at also example 2.5.

Figure 7:
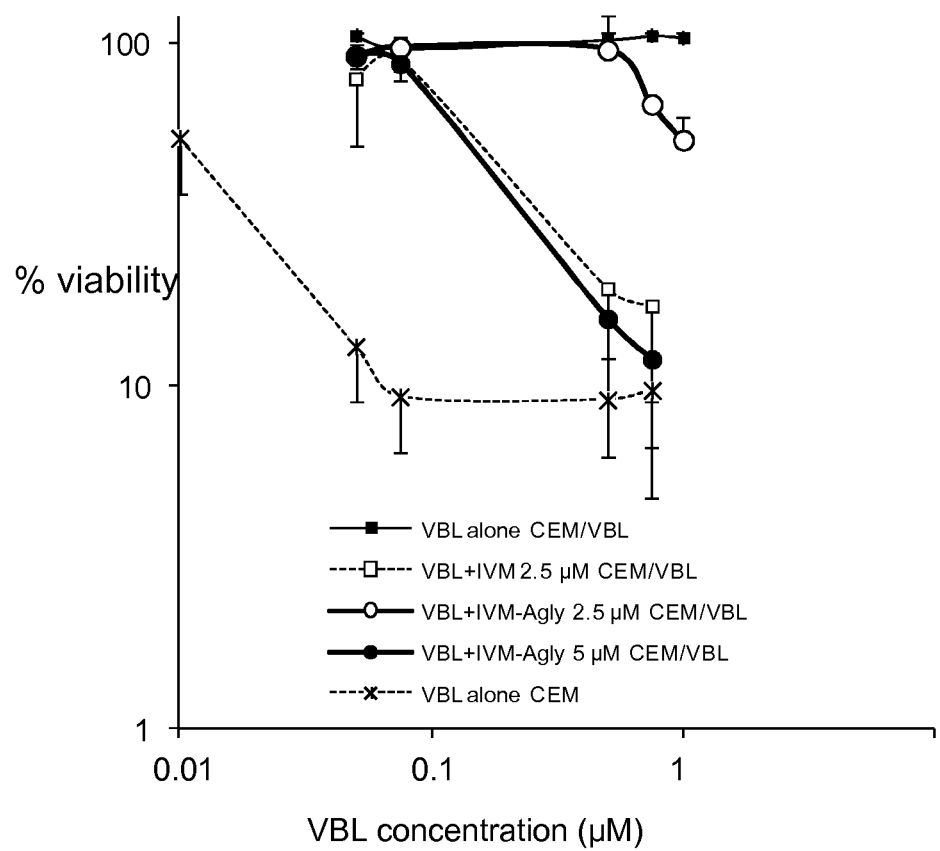

FIG. 7 illustrates the reversion of drug-resistance by ivermectin aglycone in human lymphoma parental CEM cells and in vinblastine resistant CEM/VBL cells. CEM/VBL cells were incubated 4 days with vinblastine alone from 0 to 1 µg/ml (black square), or with vinblastine from 0 to 1 µg/ml and ivermectin (IVM) at 2.5 µM (open square), or with vinblastine from 0 to 1 µg/ml and ivermectine aglycone (IVM-Agly) at 2.5 µM (open circle), or with vinblastine from 0 to 1 µg/ml and ivermectine aglycone (IVM-Agly) at 5 µM (black circle). CEM cells were incubated 4 days with vinblastine alone from 0 to 1 µg/ml (-*-). X axis represents vinblastine (VBL) concentration. Y axis represents cytotoxicity determined using the MTT test. Values are mean±S.E.M. of 2 experiments (3 wells per experiment). Look at also example 2.6.

Figure 8:
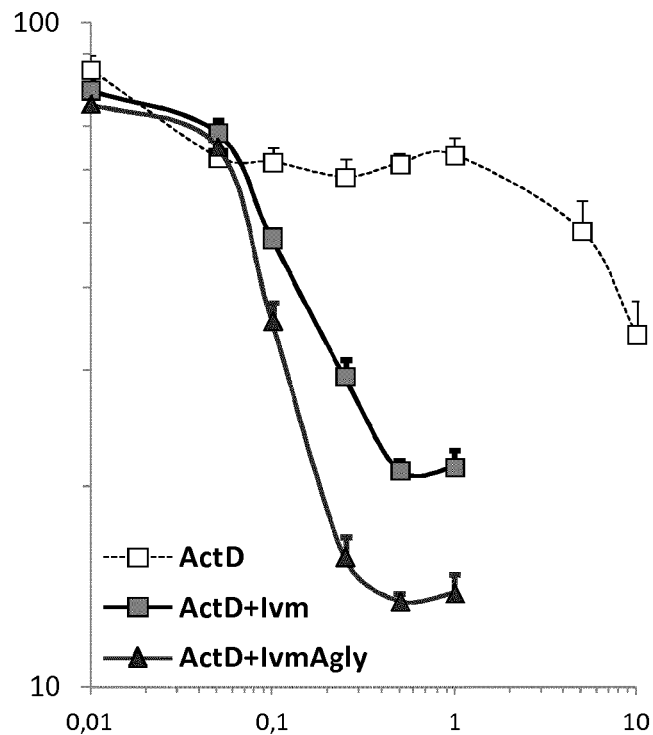

FIG. 8 illustrates the reversion of drug-resistance by ivermectin aglycone in multidrug resistant cells DC-3F/ADX which are resistant to actinomycin D. Multidrug resistant cells DC-3F/ADX were incubated 3 days with actinomycin alone from 0.01 to 10 µM (open square), or with actinomycin from 0.01 to 10 µM and ivermectin (IVM) at 5 µM (grey square) or with actinomycin from 0.01 to 10 µM and ivermectin aglycone (IVM-Agly) at 5 µM (black triangle). X axis represents actinomycin D concentration. Y axis represents cytotoxicity determined using the MTT test. Values are mean±S.E.M. of 2 experiments (3 wells per experiment). Look at also example 2.6.

Figure 9:
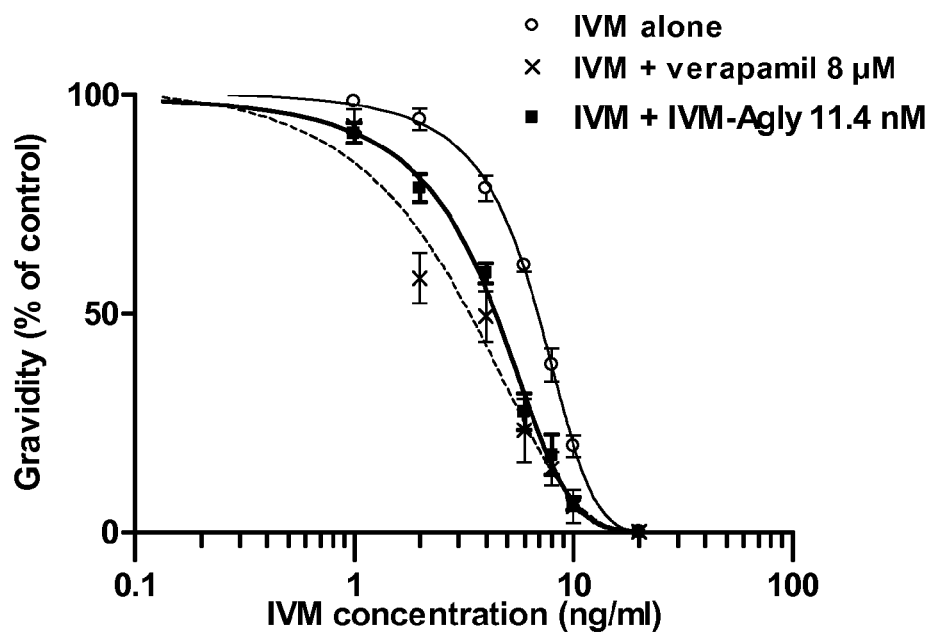

FIG. 9 shows reversion of ivermectin-resistance by ivermectin aglycone in *Caenorhabditis elegans* resistant to ivermectin. Ivermectin resistance in *C. elegans* is determined according to the protocol described in part 1.9 below. X axis represents ivermectin concentration. Y axis represents the percentage of gravidity compared to control. Gravidity was evaluated in the presence of ivermectine (IVM) alone at 0, 1, 2, 4, 6, 8, 10, 20 ng/ml (open circle), or ivermectin at 0, 1, 2, 4, 6, 8, 10, 20 ng/ml with verapamil at 8 µM (-x-), or ivermectin at 0, 1, 2, 4, 6, 8, 10, 20 ng/ml with ivermectin aglycone (IVM Agly) at 10 ng/ml (11.4 nM) (black square). Assays were performed in 3 replicates per condition treatment and the experiment was performed 3 times. Mean±S.D. Look at also example 2.7.

EXAMPLES

1. Materials and Methods
1.1 Ivermectin Aglycone Synthesis
Ivermectin aglycone (22,23-dihydroavermectin B1 aglycone) is obtained from ivermectin by acid hydrolysis (1% of sulphuric acid). Ivermectin aglycone is purified by HPLC according to the method described by Alvinerie et al. (*Ann Rech Vet*, (1987), 18, 269-274).

1.2 Ivermectin Aglycone Structure Analysis

HPLC

The protocol of HPLC experiment is as follows: the product obtained after synthesis reaction is analysed by HPLC according a modified method routinely used in the INRA laboratory. Briefly a fluorescent derivative was obtained by dissolving the eluent in N-methylimidazole and trifluoroacetic anhydride (Aldrich, Milwaukee, Wis., USA) solutions in acetonitrile. The chromatographic conditions included a mobile phase of acetic acid 2%, methanol, acetonitrile (4:32:64, v/v/v) pumped at a flow rate of 1.5 ml/min through a Supelcosil C18, 3 µm column (150×4.6 mm) (Supelco, Bellefonte, Pa., USA). Fluorescence detection (Detector RF 551, Shimadu, Kyoto, Japan) was performed at 365 nm excitation and 475 nm emission wavelength. The validation of the technique was performed (Alvinerie at al, 1993, Vet Res 24 (5): 417-21).

Mass Spectrometer

Structural characterization of the purified products was conducted on the platform Axiom of INRA/ToxAlim, on a LCQ quadrupole ion trap mass spectrometer (Thermo Finnigan, Les Ulis, France) fitted with an electrospray ionization source operated in the positive mode. The protocol of mass spectrometer assay is as follows: collected samples were introduced into the ionization source by infusion at a flow rate of 5 L/min with a syringe pump.

1.3 Cell Culture

The cells used were LLC-PK1, pig kidney epithelial cell lines, and LLC-PK1-mdr1a which are recombinant LLC-PK1 cells overexpressing murine abcb1a gene. All cell lines are available in INRA laboratory. The transfected cell line LLC-PK1-HcPgpA, which overexpress nematode *Haemonchus contortus* PgpA, was developed by R. Prichard (McGill University). Cells were cultured in medium 199 supplemented with penicillin (100 units/ml), streptomycin (100 g/ml), 10% of foetal calf serum and geneticin G418 (400 mg/1) as selecting compound for the LLC-PKI-mdr1a and LLC-PK1-HcPgpA cells. All compounds and medium are from Invitrogen, Cergy Pontoise, France. Cells were seeded on 24-well plates (Sarstedt, Orsay, France) at $2 \times 10^5$ cells/well in G418-free medium until confluence for transport activity and on 96-well plates for viability assay.

Multidrug resistant tumor cells used in the present invention were Human lymphoma parental CEM and vinblastine-resistant CEM/VLB (Zordan-Nudpo et al., 1993) and parental CEM and multidrug resistant cells DC-3F/ADX selected from spontaneously transformed DC-3F Chinese hamster lung fibroblasts on the basis of their resistance to actinomycin D (Biedler and Riehm, 1970). Both types of resistant cells overexpressed Pgp.

1.4 Animal Model

Wild-type and the Pgp knock-out mdr1ab$^{-/-}$ mice with a FVB genetic background were obtained from Taconic (NY, USA). In rodents, there are two Pgps encoded by abc1a and abc1b genes and mdr1ab$^{-/-}$ mice were deficient for the two gene products. Mice were housed at INRA's transgenic rodent facility at 22±2° C. under 12-hour light/dark cycles. Animals sampling was designed to reduce the influence of interfering parameters such as litter specificity (seven to nine different litters for a ten animals group). Mice received a standard chow diet recommended for the breeding and rearing of rodents (Harlan Teklad TRM Rat/Mouse Diet; Harlan Teklad, Gannat, France). Water and food were available ad libitum. In vivo studies were conducted in mice under European laws on the protection of animals and protocols are performed under procedure and principal for good clinical practice.

1.5 Tested Molecules

Ivermectin aglycone obtained according to the synthesis method described in part 1.1 and purified is used in all the comparative experiments of the present invention.

Ivermectin purchased from Sigma is used as inhibition standard in all the comparative experiments of the present invention.

Valspodar® was kindly provided by Novartis and is used as reference inhibitor of Pgp.

All the three aforementioned compounds are solubilised in DMSO.

1.6 Transport Tests In Vitro

Cells were cultured with rhodamine 123 (10 µM, purchased from Sigma) with or without valspodar (VSP, 5 µM). Compounds of interest were dissolved in DMSO and diluted in the medium (final DMSO concentration=0.1%) in a concentration range of 0.1-50 µM. After the 2-h incubation period, the cells were lysed and lysates were stored at −20° C. until analysis. To study the Pgp transport activity, the intracellular accumulation of fluorescent Rho 123 was determined by reading fluorescence in the cell lysates with a spectrofluorimeter (PerkinElmer LS50B, max excitation=507 nm; max emission=529 nm). Protein concentration was determined in lysates with BCA kit using bovine serum albumin as protein standard (Thermo scientific) Results were expressed as fluorescence arbitrary units after normalization to cellular protein content per well.

1.7 GABA Receptor Affinity Test

The ability of ivermectin or moxidectin or ivermectin aglycone or ivermectin monosaccharide to interact with GABA receptors is assayed by electrophysiology measurements. *Xenopus laevis* oocytes are injected with 46 nl of RNA solution, with RNA coding for $\alpha_1$, $\beta_2$ and $\gamma_2$ subunits of the GABA channel at a ratio of 10:10:50 nM. The injected oocytes are incubated in modified Barth's solution[90 mM NaCl, 3 mM KCl, 0.82 mM MgSO$_4$, 0.41 mM CaCl$_2$, 0.34 mM Ca(NO$_3$)$_2$, 100 U/ml penicillin, 100 µg/ml streptomycin and 100 µg/ml kanamycin, 5 mM HEPES pH 7.6] at 18° C. for approximately 36 h before the measurements to ensure the expression of a functional receptor.

Electrophysiological experiments are performed by the two-electrode voltage-clamp method. Measurements were done in ND96 medium containing 96 mM NaCl, 2 mM KCl, 1 mM g Cl$_2$, 1.8 mM CaCl$_2$ and 5 mM HEPES, pH 7.5, at a holding potential of −80 mV. The control current is evoked by the application of 2 µM GABA and the normalized relative potentiation of 2 µM GABA-evoked currents by increasing concentration of ivermectin, moxidectin, ivermectin aglycone, or ivermectin monosaccharide is determined as:

$$[(I_{MLs+2 \: \mu M \: GABA}/I_{2 \: \mu M \: GABA \: alone})/ (I_{(MLs+2 \: \mu M \: GABA)Max}/I_{2 \: \mu M \: GABA \: alone})] \times 100\%$$

where $I_{2 \: \mu M \: GABA}$ is the control current evoked by 2 µM GABA, $I_{MLs+2 \: \mu M \: GABA}$ is the current evoked by each drug concentration in co-applications with 2 µM GABA, and $I_{(MLs+2 \: \mu M \: GABA)Max}$ is the maximal current evoked by co-applications of drugs and 2 µM GABA. A washout period of 4 min between each GABA application is introduced, allowing receptors to recover from desensitization. Three different batches of oocytes are used to collect data for each analysis. The perfusion system is cleaned between two experiments by washing with 10% DMSO after application of MLs derivatives to avoid contamination.

1.8 In Vivo Toxicity Test

Toxicity of ivermectin and ivermectin aglycone is measured in Pgp-deficient mice. Mdr1ab$^{-/-}$ mice are injected subcutaneously with increasing doses of ivermectin or ivermectin aglycone formulated in propylene glycol/formaldehyde (60:40, v/v). Higher injected doses are 1.5 mg/kg (1.7 µmol/kg) for ivermectin and 16 mg/kg (27 µmol/kg) for ivermectin aglycone, respectively. Toxicity is evaluated during 24 h. At the end of the monitoring, plasma is collected, from the orbital sinus vein under methoxyflurane anesthesia and the mice are sacrificed for the brain collection. Blood is centrifuged at 1500 g for 10 min, and plasma is stored at −20° C. until analysis. The brains is removed, washed in saline solution, and frozen at −20° C. until analysis.

1.9 Ivermectin Resistance Assay in *Caenorhabditis elegans*

A gravid assay method, based on the development of eggs to gravid adults over a 96 hr incubation period, was used to determine the resistance with respect to ivermectin (IVM) in *C. elegans*. The eggs were collected through rinsing the *C. elegans* worms resistant to IVM (IVR10). Sixty eggs were incubated/well, in standard conditions for four days (96 hours) in order reach adulthood (gravid) in the presence of drugs as followed: ivermectin aglycone (IVM-Agly) alone at 10 ng/ml (11.4 nM); verapamil (VRP) alone at 8 µM; IVM alone: 0, 1, 2, 4, 6, 8, 10, 20 nM; IVM+VRP 8 µM: 0, 1, 2, 4, 6, 8, 10, 20 ng/ml IVM; IVM+IVM-Agly 10 ng/ml: 0, 1, 2, 4, 6, 8, 10, 20 ng/ml (0.114-22.8 nM) IVM. Assays were performed in triplicates per condition treatment and the experiment was performed 3 times.

2. Results

2.1 Ivermectin Aglycone Synthesis

Figure 1A:
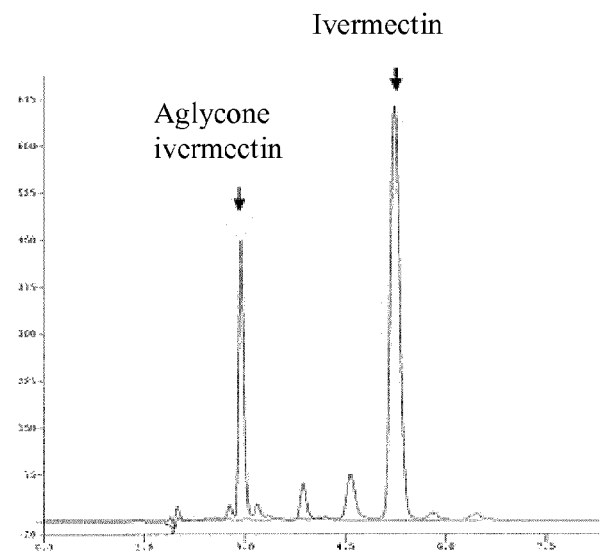
FIG. 1A represents the HPLC profile of ivermectin and ivermectin aglycone.
Figure 1B:
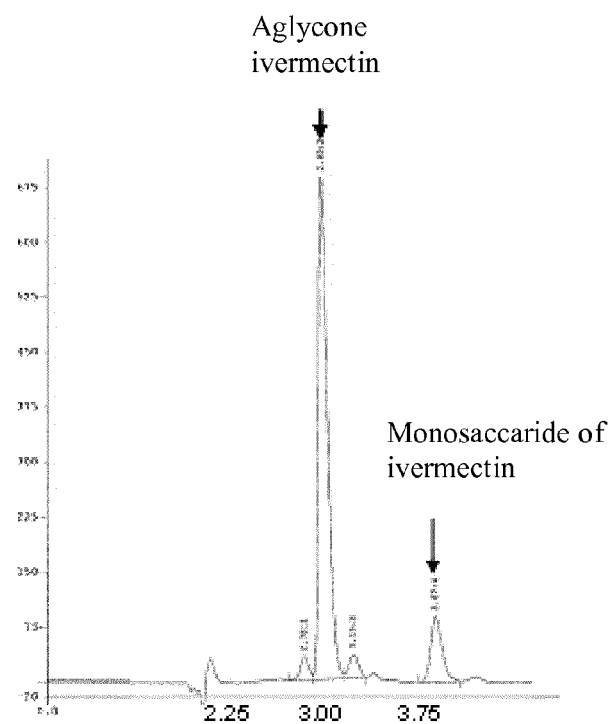
FIG. 1B represents the HPLC profile of ivermectin aglycone and monosaccharide of ivermectin.

Ivermectin aglycone is obtained from ivermectin by acid hydrolysis, which cuts the chemical bond between macrocycle and disaccharide group. The product obtained after this reaction is a mixture of about 80% ivermectin aglycone and 20% monosaccharide of ivermectin, as showed by structure profile performed by HPLC (FIGS. 1A and 1B). Ivermectin aglycone obtained by said synthesis method is characterised by a hydroxyl group on carbon C13 of macrocycle (FIG. 1B) and a 3 minutes of retention time in our chromatographic conditions, shorter than that of ivermectin (5 minutes) or that of monosaccharide derivative (4 minutes).

Figure 2:
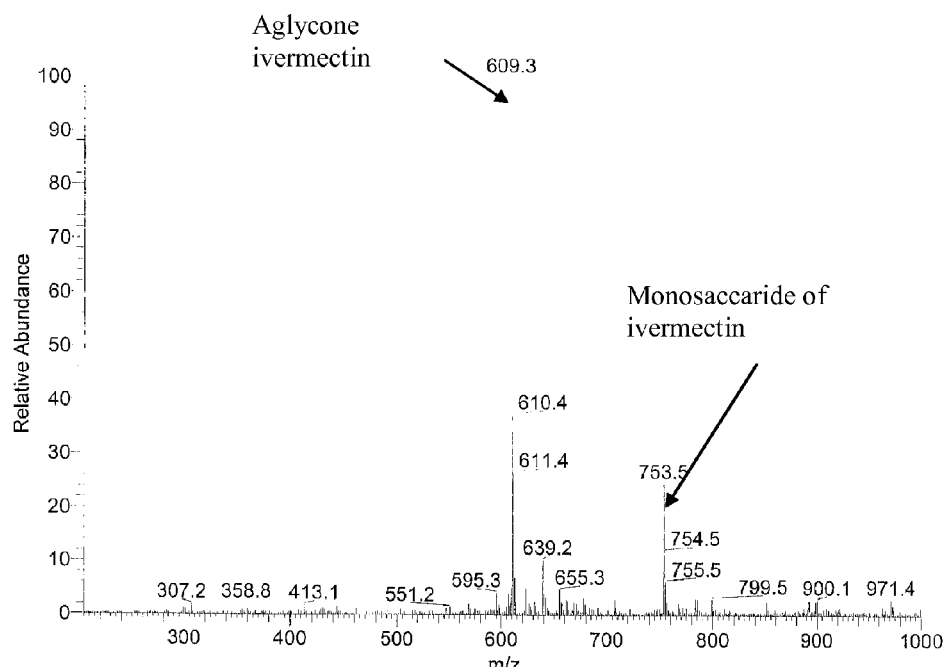
FIG. 2 represents the mass spectrometric profile of aglycone ivermectin.

The obtained product is then analysed by mass spectrometry, which confirms the presence of a mass pick at 609.3 which corresponds to ionised ivermectin aglycone (FIG. 2), while the mass pick of native ivermectin aglycone is at 586.8.

2.2 Ivermectin Aglycone Inhibitory Potency for Pgp in Cell Model

Ivermectin aglycone inhibitory potency for transport activity of Pgp is assayed in transfected cells LLCPK1-mdr1a overexpressing murine Pgp (mdr1a). Maximum inhibition has been obtained with Valspodar®, the most powerful reference inhibitor of Pgp known in the past. It is confirmed that ivermectin is an inhibitor of Pgp as powerful as Valspodar® (FIG. 3). It is also shown that ivermectin aglycone has a comparable efficacy to inhibit murine Pgp to that of ivermectin, with maximal effect ($E_{max}$) at about 10 µM (Table 1, FIG. 3).

TABLE 1

Inhibitory effect of ivermectin and ivermectin aglycone in cells overexpression murine Pgp

|  | Ivermectin | Ivermectin aglycone |
|---|---|---|
| $EC_{50}$ (µM) | 0.5 | 1.0 |
| $C_{max}$ (µM) | 5.0 | 10.0 |
| $E_{max}$ (% valspodar ®) | 88.0 | 80.0 |

$EC_{50}$: effective concentration for inhibiting 50% of transport of rhodamine 123 by murine Pgp.
$C_{max}$: concentration to obtain maximum inhibitory effect.
$E_{max}$: maximum effect compared to maximum effect obtained with 5 µM of valspodar.

2.3 Different Inhibitory Potency of Ivermectin Aglycone for Murine Pgp and Nematode Pgp Inhibitory potency of ivermectin aglycone or ivermectin for murine Pgp or nematode Pgp is respectively measured in cells LLCPK1-mdr1a, which overexpress murine Pgp (MDR1), or in cell model developed by R. Prichard, which overexpress nematode *Haemonchus contortus* Pgp: hc-pgpA. The results show that ivermectin has similar potency to inhibit mammalian Pgp ($EC_{50}$=0.5 µM) and nematode HcPgpA ($EC_{50}$=0.6 µM) (Table 2, FIGS. 4A and 4B), while ivermectin aglycone has 5 times higher inhibitory potency for parasite HcPgpA ($EC_{50}$=0.5 µM) than for mammalian Pgp ($EC_{50}$=2.5 µM). These results clearly indicated that ivermectin aglycone is more potent in inhibiting nematode HcPgpA than mammalian Pgp.

TABLE 2

Concentration of half inhibitory effect of ivermectin and ivermectin aglycone in cells overexpress Pgp

|  | EC50 µM | |
|---|---|---|
|  | Ivermectin | Ivermectin aglycone |
| Murine Pgp | 0.5 | 2.5 |
| Nematode PgpA | 0.6 | 0.5 |

2.4 Ability of Ivermectin Aglycone or Ivermectin Monosaccharide to Open GABA Receptor in Oresence of GABA.

of the ability of ivermectin aglycone or ivermectin monosaccharide to potentiate GABA action on GABA receptor, was assayed according to the protocol described in aforementioned part 1.7, and was compared with ivermectin.

The results displayed in table 4 show that ivermectine monosaccharide (IVM Monosaccharide) and ivermectine aglycone (IVM-Agly) are a weak agonist ($EC_{50}$=122.4 nM for IVM Monosaccharid and $EC_{50}$=215.1 nM for IVM-Agly) compared to ivermectin ($EC_{50}$=29 nM) (Table 3, FIG. 5). This result means that ivermectin monosaccharide and ivermectin aglycone have a much weaker neurotoxicity when compared with ivermectin, and a pharmaceutical use of ivermectin aglycone or ivermectin monosaccharide is possible.

TABLE 3

Parameters of interaction of IVM and derivatives with GABA receptors: $EC_{50}$ is the concentration needed to induce half of the maximal potentiation of GABA effect by MLs or derivatives.

| MLs | $EC_{50}$ (nM) |
|---|---|
| MOX | 5.6 ± 1.5 |
| IVM | 29.3 ± 3.4 |
| IVM Monosaccharide | 122.4 ± 20.3 |
| IVM Aglycone | 215.1 ± 12.45 |

2.5 In Vivo Toxicity of Ivermectin Aglycone

In vivo toxicity text in Pgp-deficient mice confirms that the lethal dose for ivermectin is from 0.6 to 0.8 µmol/kg, as what is described by Schinket et al. (Cell (1994) 77, 491-502). On the contrary, ivermectin aglycone does not show any toxicity when it is administered with a dose till 10 times higher than that of ivermectin (FIG. 6). This result confirms that ivermectin aglycone has a much weaker in vivo toxicity compared to ivermectin and a pharmaceutical use of ivermectin aglycone is possible.

2.6 Reversal of Multidrug Resistance by Ivermectin Aglycone in Multidrug Resistant Tumor Cells CEM/VLB cells and DC-3F/ADX cells described in aforementioned part 1.3 were plated into 96 well plates and allowed to grow for 24 h. They were then incubated 4 days with vinblastine (concentration range 0-1 µM) with or without IVM at 2.5 µM or ivermectin aglycone (IVM-Agly) at 2.5 and at 5 µM (FIG. 7); or 2 days with actinomycin D with actinomycin (concentration range 0.01-10 µM) with or without ivermectin (IVM) or ivermectin aglycone (IVM-Agly) at 5 µM (FIG. 8). Cytotoxicity was determined using the MTT test. $IC_{50}$ values were graphically determined and they represent the concentration needed for half cell survival. Fold reversal of multidrug resistance called reversion factors were the ratio of $IC_{50}$ for toxic drug alone/$IC_{50}$ for toxic drug in the presence of IVM-Agly.

IVM-Agly was able to reverse drug resistance in tumor cells overexpressing Pgp. CEM/VBL are highly resistant to VBL and cells were fully viable in 1 µM vinblastine while the parental cells are highly sensitive to VBL at concentrations below 0.001 µM. Co-incubation of VBL with IVM at 2.5 µM, or IVM-Agly at 5 µM provoke a clear left-shift of the viability cell curve (FIG. 7) demonstrating that cells are sensitized to VBL in presence of the tested compounds. In the presence of IVM at 2.5 µM the VBL $IC_{50}$ was 0.2 µM and in presence of IVM-Agly at 2.5 and 5 µM, the $IC_{50}$ values were 1 and 0.2 µM, reflecting that IVM-Agly's has similar inhibitory potency compared to that of IVM (Table 1). In addition, DC-3F/ADX viability was not altered by 1 µM actinomycin D while when combined with IVM or IVM-Agly at 5 µM actinomycin D became toxic (FIG. 8).

The results of FIG. 7, FIG. 8 and table 4 showed that the ability of ivermectin aglycone to reverse vinblastine or actinomycinD-resistance in tumor cells overexpression Pgp was of the same order of potency as ivermectin, which is potent inhibitor of MDR transporters.

TABLE 4

Comparison of IC50 and resistance factor (RF) for IVM and IVM Agly in multidrug-resistant cells

|  | IC50 (µM) | RF |
|---|---|---|
| CEM/VBL |  |  |
| VBL | Nd |  |
| VBL + IVM 2.5 µM | 0.2 |  |
| VBL + IVM-Agly 2.5 µM | 1.0 |  |
| VBL + IVM-Agly 5 µM | 0.2 |  |
| DC-3F/ADX |  |  |
| ActD | 5.0 |  |
| ActD + IVM 5 µM | 0.11 | 45 |
| ActD + IVM-Agly 5 µM | 0.08 | 62 |

Nd: not determined

2.7 Reversal of Anthelmintic Resistance by Ivermectin Aglycone in C. elegans Resistant to Ivermectin The reversal action of ivermectin aglycone (IVM-Agly) was studied on the nematode Caenorhabditis elegans resistant to ivermectin (IVR10). This strain has been previously selected under IVM pressure and it was shown to overexpressed P-gp homologue genes (James and Davey, 2009). We measured the ability of IVM-Agly to restore the development from eggs to adults which has been delayed by the ivermectin effect on the IVR10 strain, and compared its effect to that of the verapamil (VRP) reversal effect.

The resistance with respect to invermectin in C. elegans is measured according to the protocol described in aforementioned part 1.9.

IVM blocked the development of C. elegans IVR10 eggs at a concentration averaging 10 nM confirming that this strain is resistant to IVM. The $IC_{50}$ for IVM was 6.8±0.2 ng/ml (7.8±0.2 nM). verapamil, a known Pgp-reversing agent, at 8 µM had no effects on the development of the C. elegans when alone, and was able to restore the development of worms stopped in the presence of IVM. The curve of IVM efficacy was thus shifted to the left with the $IC_{50}$ of IVM reduced to 3.2±0.5 ng/ml (3.6±0.6 nM) when compared to IVM alone (FIG. 9, Table 5). IVM-Agly at 10 ng/ml was also able to significantly decrease the $EC_{50}$ of IVM to 4.5±0.3 ng/ml (5.1 nM, Table 5), and IVM-Agly alone at 10 ng/ml had no effects on the development of the C. elegans suggesting that IVM-Agly also reverse a Pgp-mediated drug resistance.

The lower $EC_{50}$ for ivermectin efficacy in IVM resistant C. elegans determined in presence of IVM-Agly testifies that IVM-Agly is able to partly reverse IVM resistance. Based on the fact that verapamil are well-known inhibitors of Pgp, their effects comparable to the one produced by IVM-Agly suggest that the IVM-Agly reversion also occurs through inhibition of Pgp-like transporters.

TABLE 5

Comparison of $IC_{50}$ and resistance factor (RF) for the reference reversal agent valspodar and verapamil and IVM-Agly in ivermectin-resistant C. elegans

|  | $IC_{50}$ (nM) | RF |
|---|---|---|
| IVM alone | 7.8 ± 0.2 |  |
| IVM + verapamil (4 µM) | 3.6 ± 0.6 | 2.1 |
| IVM + IVM-agly (11.4 nM) | 5.1 ± 0.3 | 1.5 |

The invention claimed is:
1. A pharmaceutical composition comprising a compound of formula Ia

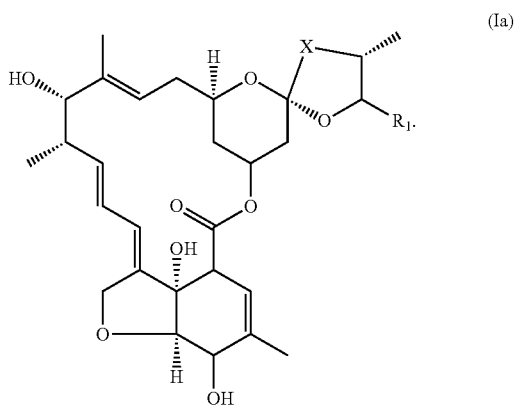

(Ia)

wherein
  R$_1$ is selected from the group consisting of —CH(CH$_3$)$_2$ and —CH(CH$_3$)CH$_2$CH$_3$,
  a second active ingredient selected from the group consisting of a macrocyclic lactone antiparasitic agent, an antitumoral agent, an antiviral agent, an antibacterial agent, and an antifungal agent, wherein the second active ingredient is a compound other than a compound of formula Ia;
  and,
  a pharmaceutically acceptable carrier, wherein the compound is present in the composition in an amount at least equal to the amount of the second active ingredient in the composition.

2. The pharmaceutical composition according to claim 1 wherein the second active ingredient is an antiparasitic agent.

3. The pharmaceutical composition according to claim 2, wherein the second active ingredient is selected from the group consisting of avermectins and milbemycins.

4. The pharmaceutical composition according to claim 1, wherein the second active ingredient selected from the group consisting of abamectin, doramectin, eprinomectin, and a milbemycin.

5. The pharmaceutical composition according to claim 1, wherein said composition consists of the compound of formula I(a), the second active ingredient, and a pharmaceutically acceptable carrier.

6. A method for the treatment of infections, comprising administering to a subject in need of such treatment a composition according to claim 1.

7. The method according to claim 6, wherein the second active ingredient is an antiparasitic agent.

8. The method according to claim 7, wherein the second active ingredient is selected from the group consisting of avermectins and milbemycins.

9. The method according to claim 7, wherein the second active ingredient is selected from the group consisting of abamectin, doramectin, eprinomectin, and a milbemycin.

10. A method for the treatment of cancers that are resistant to chemotherapeutic agents, wherein the cancers express ATP-binding cassette (ABC) transporters, comprising administering to a subject in need thereof a composition according to claim 1 in combination with an antitumoral agent.

* * * * *